United States Patent
O'Connor

(10) Patent No.: US 8,922,380 B2
(45) Date of Patent: Dec. 30, 2014

(54) WATER RESISTANT DRUG INFUSION HOUSING WITH PRESSURE DIFFERENTIAL SENSOR

(71) Applicant: Sean M. O'Connor, West Chester, PA (US)

(72) Inventor: Sean M. O'Connor, West Chester, PA (US)

(73) Assignee: Animas Corporation, West Chester, PA (US)

( * ) Notice: Subject to any disclaimer, the term of this patent is extended or adjusted under 35 U.S.C. 154(b) by 78 days.

(21) Appl. No.: 13/628,140

(22) Filed: Sep. 27, 2012

(65) Prior Publication Data
US 2013/0076518 A1    Mar. 28, 2013

Related U.S. Application Data

(60) Provisional application No. 61/539,585, filed on Sep. 27, 2011.

(51) Int. Cl.
| | | |
|---|---|---|
| *G08B 21/00* | (2006.01) | |
| *A61M 5/168* | (2006.01) | |
| *A61M 5/142* | (2006.01) | |

(52) U.S. Cl.
CPC . *A61M 5/16854* (2013.01); *A61M 2005/14264* (2013.01); *A61M 2205/18* (2013.01); *A61M 5/14244* (2013.01)
USPC .................... 340/626; 340/573.1; 340/539.12

(58) Field of Classification Search
CPC combination set(s) only.
See application file for complete search history.

(56) References Cited

U.S. PATENT DOCUMENTS

| | | | | |
|---|---|---|---|---|
| 6,458,102 | B1 * | 10/2002 | Mann et al. | 604/131 |
| 8,454,562 | B1 * | 6/2013 | Sims | 604/151 |
| 2004/0065615 | A1 * | 4/2004 | Hooper et al. | 210/650 |
| 2004/0085215 | A1 | 5/2004 | Moberg et al. | |
| 2005/0177108 | A1 * | 8/2005 | Paul et al. | 604/131 |
| 2008/0088483 | A1 * | 4/2008 | Hellwig | 340/945 |
| 2009/0299290 | A1 * | 12/2009 | Moberg | 604/151 |
| 2011/0021993 | A1 * | 1/2011 | Bar-Haim et al. | 604/153 |
| 2011/0160670 | A1 * | 6/2011 | Kallesoe Nielsen et al. | 604/151 |
| 2011/0190704 | A1 * | 8/2011 | Lynch et al. | 604/152 |
| 2012/0157919 | A1 * | 6/2012 | Butterfield | 604/151 |
| 2013/0338576 | A1 * | 12/2013 | O'Connor et al. | 604/67 |
| 2013/0338635 | A1 * | 12/2013 | O'Connor et al. | 604/506 |

FOREIGN PATENT DOCUMENTS

WO    2009/013735 A1    1/2009

OTHER PUBLICATIONS

International Search Report issued in Application No. PCT/US2012/057303, mailed Jan. 30, 2013, 4 pages.

* cited by examiner

*Primary Examiner* — Travis Hunnings

(57) ABSTRACT

Described is drug infusion device with one or more vents that permit the passage of gas between the exterior and interior of the device's housing. In one embodiment the device may include multiple interior chambers of differing volume and pressure sensors placed between them, while vents to ambient pressure are included in each chamber. According to this exemplary structure, the readings from the pressure sensor may be used to determine malfunctions in the venting of the device and/or changes in pressure that could cause the unintended delivery of medication.

5 Claims, 1 Drawing Sheet

WATER RESISTANT DRUG INFUSION HOUSING WITH PRESSURE DIFFERENTIAL SENSOR

CROSS REFERENCE TO RELATED APPLICATIONS

This application relates to U.S. patent application Ser. No. 61/539,585, filed Sep. 27, 2011; all applications are herein incorporated by reference in their entireties.

FIELD OF THE INVENTION

The present invention relates, in general, to drug delivery devices and, more particularly, to systems and methods for detecting pressure differentials in portable drug infusion devices.

BACKGROUND OF THE INVENTION

The use of drug delivery devices for various types of drug therapy is becoming more common as the automated infusion of a drug may provide more reliable and more precise treatment to a patient.

Diabetes is a major health concern, as it can significantly impede on the freedom of action and lifestyle of persons afflicted with this disease. Typically, treatment of the more severe form of the condition, Type I (insulin-dependent) diabetes, requires one or more insulin injections per day, referred to as multiple daily injections. Insulin is required to control glucose or sugar in the blood, thereby preventing hyperglycemia that, if left uncorrected, can lead to ketosis. Additionally, improper administration of insulin therapy can result in hypoglycemic episodes, which can cause coma and death. Hyperglycemia in diabetics has been correlated with several long-term effects of diabetes, such as heart disease, atherosclerosis, blindness, stroke, hypertension, and kidney failure.

The value of frequent monitoring of blood glucose as a means to avoid or at least minimize the complications of Type I diabetes is well established. Patients with Type II (non-insulin-dependent) diabetes can also benefit from blood glucose monitoring in the control of their condition by way of diet and exercise. Thus, careful monitoring of blood glucose levels and the ability to accurately and conveniently infuse insulin into the body in a timely manner is a critical component in diabetes care and treatment.

To more effectively control diabetes in a manner that reduces the limitations imposed by this disease on the lifestyle of the affected person, various devices for facilitating blood glucose (BG) monitoring have been introduced. Typically, such devices, or meters, permit the patient to quickly, and with a minimal amount of physical discomfort, obtain a sample of their blood or interstitial fluid that is then analyzed by the meter. In most cases, the meter has a display screen that shows the BG reading for the patient. The patient may then dose theirselves with the appropriate amount, or bolus, of insulin. For many diabetics, this results in having to receive multiple daily injections of insulin. In many cases, these injections are self-administered.

Due to the debilitating effects that abnormal BG levels can have on patients, i.e., hyperglycemia, persons experiencing certain symptoms of diabetes may not be in a situation where they can safely and accurately self-administer a bolus of insulin. Moreover, persons with active lifestyles find it extremely inconvenient and imposing to have to use multiple daily injections of insulin to control their blood sugar levels, as this may interfere or prohibit their ability to engage in certain activities. For others with diabetes, multiple daily injections may simply not be the most effective means for controlling their BG levels. Thus, to further improve both accuracy and convenience for the patient, insulin infusion pumps have been developed.

Insulin pumps are generally devices that are worn on the patient's body, either above or below their clothing. Because the pumps are worn on the patient's body, a small and unobtrusive device is desirable. Some devices are waterproof, to allow the patient to be less inhibited in their daily activities by having to remove their drug infusion device while showering, bathing, or engaging in various activities that might subject their infusion device to moister, such as swimming. In such devices, it would be desirable to have a structure and method for verifying proper function of venting system within the device, since vents are typically passive devices that have no means for self-diagnostic checks to verify function has been compromised (i.e. intentional or unintentional obstruction of vent opening(s)). Further, it would be desirable to be able to alert the user of abnormal pressure differentials within their device that may cause erratic or unintentional drug delivery. Finally, it would be desirable for a drug infusion device to incorporate means for detecting the altitude at which the device is located, to avoid problems associated with air travel and sporting activities such as mountain climbing, skydiving, etc. that patients may wish to engage in without having to forego the use of their drug infusion device for concerns over erratic or unintentional drug delivery due to rapid pressure changes in and around the device.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF ILLUSTRATIVE EMBODIMENTS OF THE INVENTION

In an exemplary embodiment, the invention is directed to structures and methods for detecting pressure differentials between the compartment that houses the drug reservoir of a portable drug infusion pump and the external environment (atmosphere).

Some portable infusion pumps are designed to be waterproof. This is an attractive feature for people with active lifestyles who benefit from continuous drug infusion (i.e. infusion of insulin for people with diabetes). Such devices must be designed with sealed enclosures/housings to prevent ingress of water. To avoid the development of pressure differentials between the external environment and the sealed compartment that houses the drug reservoir, most waterproof pumps incorporate hydrophobic vents that allow passage of air, but not fluids (within certain limitations of pressure differential).

Most portable drug infusion pump reservoirs are similar in design to that of a standard syringe. Therefore, the reservoir is typically comprised of two major components; a cylindrical barrel, with a connector integrated into the distal end for attachment of an infusion line set, and a movable plunger with an elastomer seal. The plunger is inserted into the open proximal end of the barrel to form a closed volume. To deliver drug, a mechanically driven piston is advanced forward, which in turn advances the cartridge plunger forward, reducing the internal volume of the cartridge, thus displacing fluid. Typically, the piston (part of the durable device) is not mechanically interlocked with the cartridge plunger because there is no need to retract the plunger once the cartridge has been filled and subsequently installed in the pump.

Because the pump piston is not interlocked with the cartridge plunger, there is a risk of unintentional delivery of drug if a positive pressure differential were to develop between the chamber that houses the reservoir and the external environment (location of infusion site). A positive pressure differential would impart a resultant force on the plunger which is directly proportional to the cross-sectional area of the drug reservoir's internal volume. If the resultant force exceeds the sustaining force of the cartridge plunger it will advance the plunger forward and thus deliver drug.

Figure 1:
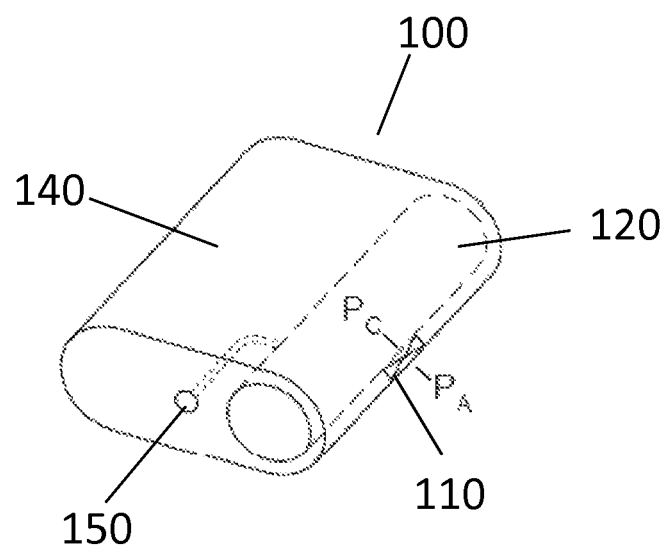
FIG. 1 illustrates an exemplary embodiment of an drug infusion device having a pressure sensor for detecting pressure differentials between a sealed drug reservoir and the interior of the pump housing.

An embodiment of the present invention is depicted in FIG. 1. An external infusion pump 100 with a waterproof or water-resistant housing may be an ambulatory infusion pump that can deliver insulin through an infusion set of the types known in the art, permitting subcutaneous infusion of the desired medicine. Typical of such devices is the Animas 2020® and OneTouch Ping® insulin delivery systems, manufactured and sold by Animas Corporation of West Chester, Pa.

Although the present illustrative embodiment of the invention relation to the infusion of insulin, other medicines can be infused in this or other, alternative embodiments of the invention. Features of the pump 100 may include, without limitation, basal programs, bolus delivery programs, bolus calculation estimators, limit alarms, reminders, visual, vibratory and auditory alarm indications, pump operation logging, and optionally, a food database to assist in calculating meal carbohydrate amounts. Illustratively, the pump 100 may communicate via a cable or wirelessly to a personal computer ("PC") to upload pump data and download of configuration settings and personal data from the PC to the pump. The PC may include software for maintaining or storing logs, displaying pump data in text or graphical format and may provide analysis to the user and/or healthcare professionals.

Power to the pump 100 can be supplied by a standard lithium or alkaline AA battery located inside of the pump 100. The pump 100 generally includes a display screen (not shown) for displaying information to the user in the form of a user interface and a speaker, vibrator, or other features known in the art to provide audible and tactile indications to the patient. So that the pump user may interact with the user interface, control devices, such as buttons, are included in the construction of the pump 100.

The pump may be configured with a display screen for providing the patient with information regarding the time, battery level, insulin level and current delivery information, as well as to provide access to a menu-driven user interface and status screens summarizing major pump operations such as basal activity, bolus activity, daily delivery totals, combo bolus activity, temporary basal activity and pump configuration codes and, additionally, any alarm conditions that the pump detects. Within the context of the present invention, it has been found to be desirable to incorporate pressure sensors within the housing 100 of the drug infusion device, to notify the user if the pump experiences environmental conditions that may affect the performance of the pump and possibly affect the actual amount of drug being delivered. In an illustrative embodiment of the invention, therefore, the drug infusion devices disclosed herein is configured to In one embodiment, the disclosed invention is a pump 100 with sealed housing that incorporates a differential pressure sensor 110 within the enclosure. The sensor 110 may be located in an exterior wall of the housing or in an interior wall that isolates the compartment that houses the drug reservoir 120 from the remainder of the internal volume of the pump. The differential pressure sensor 110 is configured to be in communication with a microprocessor (not shown) that interprets the signals received from the differential pressure sensor 110 and to create an alert that can be displayed on the device's screen (if so equipped) or communicated to the patient audibly or in a tactile manner using a speaker (or equivalent audio generation device) or vibrator. Such an alert (or alarm) would be triggered when the differential pressure sensor 110 provides signals to the microprocessor that meet certain predefined parameters.

An infusion device as described may permit a method to verify proper function of the venting system. Vents are passive devices that typically have no means for self-diagnostic checks to verify function has been compromised (i.e. intentional or unintentional obstruction of vent opening(s)). The device may also alert the user (i.e. patient) of an increasing pressure differential prior to reaching a level that could result in unintentional delivery of drug. As well, if absolute pressure sensors are used (versus differential pressure sensor), the system could also double as an altimeter. This could be an attractive feature for end users with active life-styles (who were similarly attracted to a waterproof pump). Other benefits and advantages may exist, as those skilled in the art will recognize that detection of pressure differentials within the infusion device and/or the device being able to sense its altitude can provide for the implementation of a variety of features.

FIG. 1 illustrates a simplified view of a drug infusion device 100. The device may include a housing 110 with a sealed drug reservoir chamber 120 therein. The drug reservoir chamber may include a vent 150 to the atmosphere. In one embodiment of the invention, a pressure sensor 110 of the types well-known in the art is disposed in a manner that permits the measurement of the pressure differential between the drug reservoir chamber 120 and an adjacent compartment 140 of the interior of the drug housing. Although simplified for purposes of illustration, many drug infusion devices include multiple chambers within the housing and venting schemes to ensure pressure stabilization between them. Such schemes often include vents and membranes that permit gases to flow therethrough but inhibit the passage of moisture to maintain the waterproof or water resistant integrity of the device.

Figure 2:
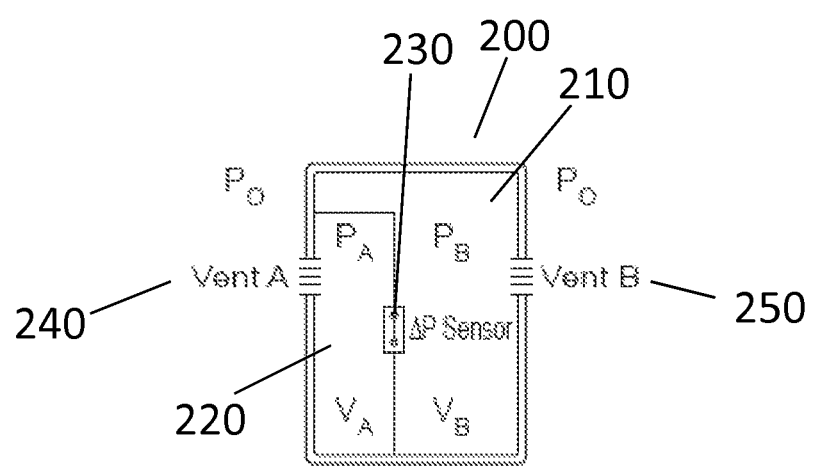
FIG. 2 illustrates an exemplary embodiment of a drug infusion device according to the present invention schematically.

FIG. 2 shows the simplified interior of the device by way of an illustrative schematic. As shown, the simplified pump includes a housing 210 with multiple chambers 210, 210, each of which is separately vented to the atmosphere via vents 240, 250. Between the chambers a pressure sensor 230 is disposed. This design permits the detection of pressure differences between the chambers and the atmosphere and can allow for the creation of alerts or alarms to the user when certain preset-conditions are met.

Pressure sensors applicable for use in the various embodiments of the invention may include, but are not limited to, piezo-type sensors and MEMS sensors. They are generally preferable due to their small size and reliability. By monitoring the differential between the chambers within the housing, such as the sealed drug reservoir chamber and the external environment (ambient pressure), the device may be configured to trigger one or more of audible, tactile, or visual alarms. The user/patient may then be able to identify the source of the pressure differential and correct it or manually disconnect the drug infusion device to ensure that there is no unintended delivery of drug from what is typically a drug cartridge disposed in the sealed drug reservoir chamber. This method permits the preemptive detection of malfunctioning venting or another condition, rather than waiting until a degree of unintentional and possible harmful drug delivery has occurred.

Since some pressure sensors suitable for use according to the present invention are susceptible to damage or malfunction from such things as moisture and radiation (UV typically, but also IR), it is desirable for the pressure sensors to be mounted internal with respect to the exterior housing of the device. It has been found that the sensor may be particularly effective when positioned between two internal chambers of the device that are of different volume, as shown in FIG. 2, and both of the internal chambers 210, 220 are independently vented to ambient pressure.

Further, it is desirable that any differential pressure sensor used be capable of communicating with a microprocessor or other electronic device that controls and/or monitors the drug delivery device. This permits the user or manufacturer to program predetermined conditions into the microprocessor that will trigger an alarm when certain conditions are met—such a abnormal pressure differentials that indicate blockage of the housing vents, extremely low pressure such as might be encountered during airline depressurization, etc.

It will be recognized that equivalent structures may be substituted for the structures illustrated and described herein and that the described embodiment of the invention is not the only structure, which may be employed to implement the claimed invention. In addition, it should be understood that every structure described above has a function and such structure can be referred to as a means for performing that function. While embodiments of the present invention have been shown and described herein, it will be obvious to those skilled in the art that such embodiments are provided by way of example only. Numerous variations, changes, and substitutions will now occur to those skilled in the art without departing from the invention.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method, comprising:
providing a drug infusion device having a housing with at least one internal chamber and at least one vent in communication with the atmosphere and the internal chamber;
providing a differential pressure sensors for determining the atmospheric pressure in the internal chamber and of the atmosphere external to the housing;
sensing a pressure differential;
communicating the pressure differential to a microprocessor; and
generating an audible, visual, or tactile signal when the pressure differential meets certain predefined conditions;
wherein the at least one vent is configured to inhibit or prevent the ingress of water into the housing.

2. The method of claim 1 wherein the housing has at least two chambers.

3. The method of claim 2 wherein the both of the at least two chambers are vented to the atmosphere.

4. The method of claim 2 or 3 wherein a differential pressure sensor is disposed to be in communication with each of the at least two chambers.

5. The method of claim 2 or 3 wherein a differential pressure sensor is disposed to be in communication with at least one chamber and the external atmosphere.

\* \* \* \* \*